(12) United States Patent
Chi et al.

(10) Patent No.: US 7,713,634 B2
(45) Date of Patent: May 11, 2010

(54) NON-LINEAR SILICON COMPOUND, METHOD OF MANUFACTURING OLIGOMER PROBE ARRAY USING THE SAME, SUBSTRATE FOR OLIGOMER PROBE ARRAY WITH THE SAME, AND OLIGOMER PROBE ARRAY WITH THE SAME

(75) Inventors: Sung-min Chi, Hwaseongi-si (KR);
Jung-hwan Hah, Hwaseong-si (KR);
Kyoung-seon Kim, Suwon-si (KR);
Won-sun Kim, Suwon-si (KR);
Sang-jun Choi, Seoul (KR);
Man-hyoung Ryoo, Hwaseong-si (KR)

(73) Assignee: Samsung Electronics Co., Ltd., Suwon-Si (KR)

( * ) Notice: Subject to any disclaimer, the term of this patent is extended or adjusted under 35 U.S.C. 154(b) by 448 days.

(21) Appl. No.: 11/835,630

(22) Filed: Aug. 8, 2007

(65) Prior Publication Data

US 2008/0057322 A1    Mar. 6, 2008

(30) Foreign Application Priority Data

Aug. 14, 2006  (KR) .................... 10-2006-0076909

(51) Int. Cl.
*B32B 9/04*    (2006.01)
*B32B 13/04*   (2006.01)
*G01N 33/00*   (2006.01)
*C07H 21/04*   (2006.01)

(52) U.S. Cl. .................. 428/446; 436/72; 536/24.3

(58) Field of Classification Search ................ 428/446; 436/72; 536/24.3
See application file for complete search history.

(56) References Cited

U.S. PATENT DOCUMENTS

| 5,919,523 | A | 7/1999 | Sundberg et al. |
| 6,677,163 | B1 | 1/2004 | Boukherroub et al. |
| 6,773,888 | B2 | 8/2004 | Li et al. |
| 6,808,908 | B2 | 10/2004 | Yao et al. |
| 6,979,728 | B2 | 12/2005 | Bradley et al. |
| 2002/0103348 | A1 | 8/2002 | Sato et al. |
| 2004/0234788 | A1 | 11/2004 | Li et al. |

FOREIGN PATENT DOCUMENTS

| JP | 2001-100417 | 4/2001 |
| KR | 2003-0061523 | 7/2003 |

OTHER PUBLICATIONS

English Abstract Publication No. 1020030061523.
English Abstract Publication No. 2001-100417.
Korean Notice of Allowance Sep. 5, 2007-066939028; Dec. 10, 2007.

*Primary Examiner*—Jezia Riley
(74) *Attorney, Agent, or Firm*—F. Chau & Associates, LLC

(57) ABSTRACT

A non-linear silicon compound is provided. The non-linear silicon compound may be a non-linear aromatic compound used as a linker for manufacturing an oligomer probe array. The non-linear silicon compound may reduce self-aggregation so as to form a stable and uniform monolayer. As a result, upon hybridization analysis, the fluorescent intensity may be increased.

25 Claims, 2 Drawing Sheets

NON-LINEAR SILICON COMPOUND, METHOD OF MANUFACTURING OLIGOMER PROBE ARRAY USING THE SAME, SUBSTRATE FOR OLIGOMER PROBE ARRAY WITH THE SAME, AND OLIGOMER PROBE ARRAY WITH THE SAME

CROSS REFERENCE TO RELATED APPLICATION

This application claims priority from Korean Patent Application No. 10-2006-0076909 filed on Aug. 14, 2006, the disclosure of which is hereby incorporated by reference herein in its entirety.

BACKGROUND OF THE INVENTION

1. Technical Field

The present disclosure relates to a non-linear silicon compound, a method of using the same, and to an oligomer probe array with the same.

2. Description of the Related Art

An oligomer probe array is a tool that is widely used for genetic expression profiling, genotyping, detection of mutations, such as, for example, Single Nucleotide Polymorphism (SNP), and polymorphism, analysis of protein and peptide, potential screening in medicine, development and production of new medicines, and the like.

A linker that is used for manufacturing an oligomer probe array may be introduced to allow an interactions between an oligomer probe and a target sample, for example, hybridization and to solve a difficulty in which the oligomer probe is not directly coupled to a surface of a substrate. Up to now, linear silane compounds, such as aminopropyltriethoxysilane, 4-hydroxy-N-(3-(triethoxysilyl)propyl)butanamide, and the like, have been used.

Moreover, in the existing linear silane compounds, as self aggregation readily occurs, it may be difficult to form a uniform monolayer. The reason for the above-mentioned difficulty in forming a uniform monolayer may be because the linear silane compound may be significantly affected by a solvent upon a sol-gel reaction. Accordingly, there is a need for a silicon compound that can reduce self aggregation so as to form a uniform monolayer.

SUMMARY OF THE INVENTION

Embodiments of the invention provide a silicon compound that can form a stable and uniform monolayer.

Embodiments of the invention provide a method of manufacturing an oligomer probe array using the silicon compound.

Embodiments of the invention provide a substrate for an oligomer probe array with the silicon compound.

Embodiments of the invention provide an oligomer probe array with the silicon compound.

In accordance with an exemplary embodiment of the invention, a silicon compound that is represented by the following formula is provided.

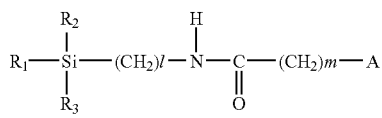

In the formula, A is an aromatic group selected from a group consisting of

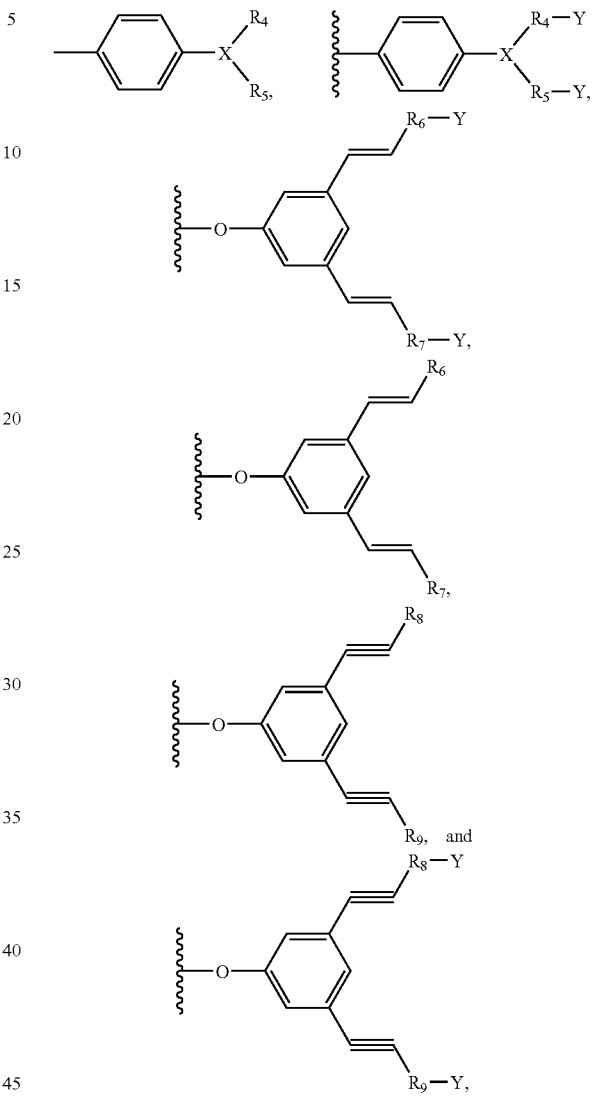

X is —O—, —N—, or —S—, each of $R_1$, $R_2$, and $R_3$ is one selected from a group consisting of —H, —$CH_3$, —($OCH_3$), —($OC_2H_5$), and a halogen, and at least one of $R_1$, $R_2$, and $R_3$ is —($OCH_3$), —($OC_2H_5$), or a halogen, each of $R_4$ and $R_5$ is one selected from a group consisting of —H, —$(CH_2)_n$—OH, —$(CH_2)_n$—$NH_2$, and $(CH_2)_n$—$SH_2$, and $R_4$ and $R_5$ may be identical or different, each of $R_6$, $R_7$, $R_8$, and $R_9$ is one selected from a group consisting of —$(CH_2)_n$—OH, —$(CH_2)_n$—$NH_2$, and —$(CH_2)_n$—$SH_2$, and $R_6$ and $R_7$ may be identical or different, and $R_8$ and $R_9$ may be identical or different, Y is a photodegradable group or an acid degradable group, and l is 2 to 10, m is 1 to 5, and n is 1 to 5.

In some exemplary embodiments of the invention a method of manufacturing an oligomer probe array using a silicon compound is provided. The method includes providing a substrate, forming an active film on the substrate, and forming a silicon compound film on the substrate.

In some exemplary embodiments of the invention a substrate for an oligomer probe array is provided. The substrate for the oligomer probe array includes a substrate, an active film on the substrate, and a linker formed of a silicon compound on the active film.

In some exemplary embodiments of the invention an oligomer probe array is provided. The oligomer probe array includes a substrate, an active film on the substrate, a linker formed of a silicon compound on the active film, and an oligomer probe coupled to the linker.

BRIEF DESCRIPTION OF THE DRAWINGS

Exemplary embodiments of the present invention can be understood in more detail from the following description taken in conjunction with the attached drawings in which.

Figure 1:
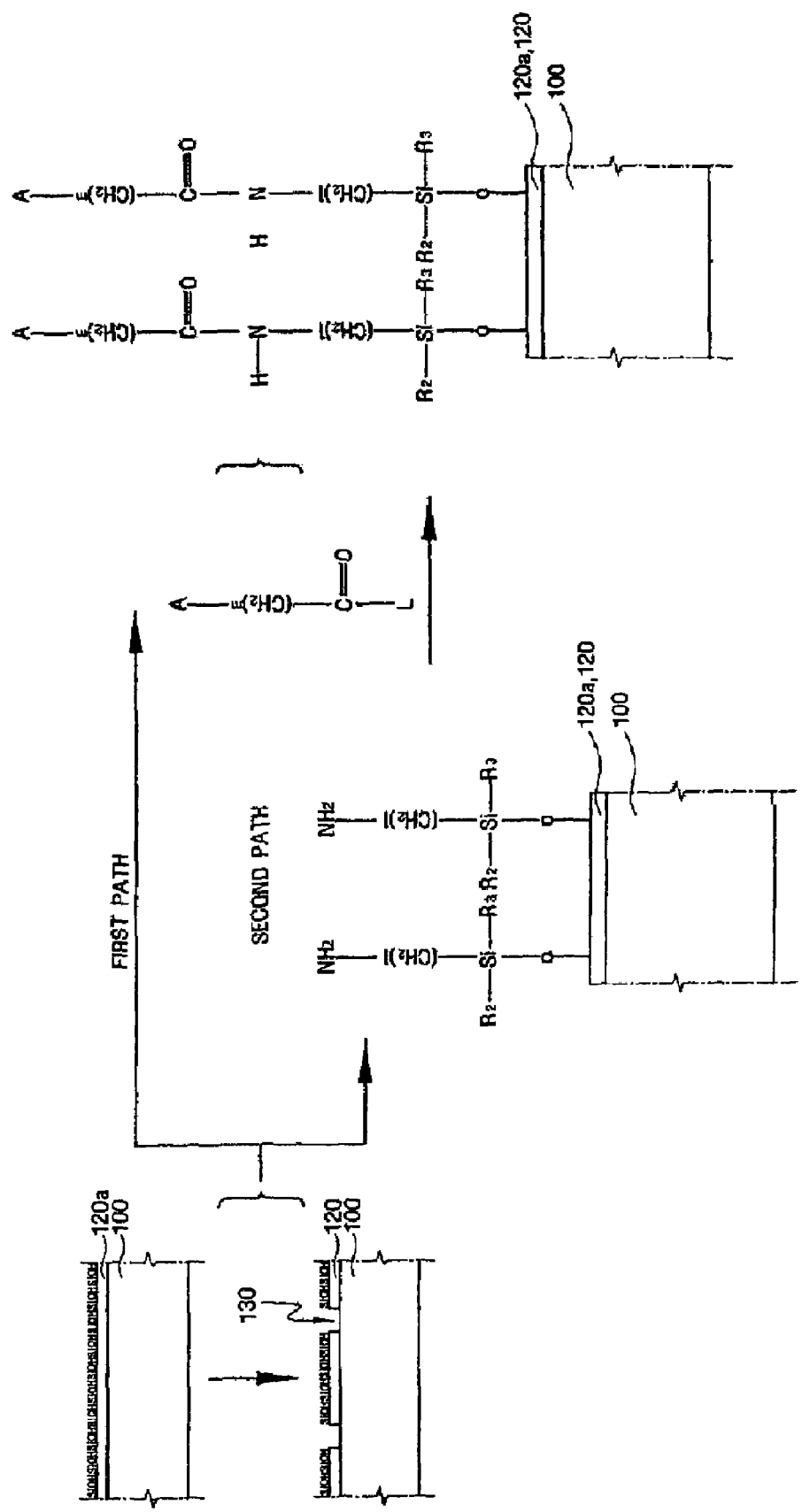
FIG. 1 is a schematic view showing a step of forming a linker of an oligomer probe array using a non-linear silicon compound according to an exemplary embodiment of the invention.

DESCRIPTION OF THE PREFERRED
EMBODIMENTS OF THE INVENTION

The present invention may, however, be embodied in many different forms and should not be construed as being limited to the embodiments set forth herein.

In the embodiments of the invention, detailed description of known device structures and techniques incorporated herein will be omitted when it may make the subject matter of the present invention unclear.

The terminology used herein is for the purpose of describing particular embodiments only and is not intended to be limiting of the invention. As used herein, the singular forms "a", "an" and "the" are intended to include the plural forms as well, unless the context clearly indicates otherwise. It will be further understood that the terms "comprises" and/or "comprising," when used in this specification, specify the presence of stated features, integers, steps, operations, elements, and/or components, but do not preclude the presence or addition of one or more other features, integers, steps, operations, elements, components, and/or groups thereof. As used herein, the term "and/or" includes any and all combinations of one or more of the associated listed items. Like numbers refer to like elements throughout.

The embodiments described herein will be described with reference to cross-sectional views and/or schematic views as illustrations of the invention. The illustrations may be changed according to a manufacturing technology and/or a tolerance. Accordingly, the embodiments of the invention are not limited to specified examples in the drawings, but may include changes according to a manufacturing process. In addition, in the drawings, for convenience of explanation, the individual parts may be adjusted to have a recognizable size.

A silicon compound according to an exemplary embodiment of the invention is a compound represented by SN-LS. Here, SN represents a silane group, and LS represents a linking and spacer group.

In the silicon compound according to an exemplary embodiment of the invention, LS may be a non-linear aromatic compound. For example, LS may be represented by the following formula.

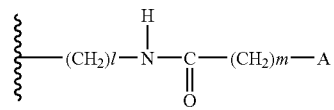

In the formula, l is 2 to 10, and m is 1 to 5. A represents a functional group that can be directly or indirectly coupled to an oligomer probe, for example, a compound that has —OH, —NH$_2$, —SH$_2$, and the like, or is degraded by light or acid so as to form the functional group. Indirect coupling means coupling through a different intermediate linker.

For example, A is an aromatic group selected from a group consisting of

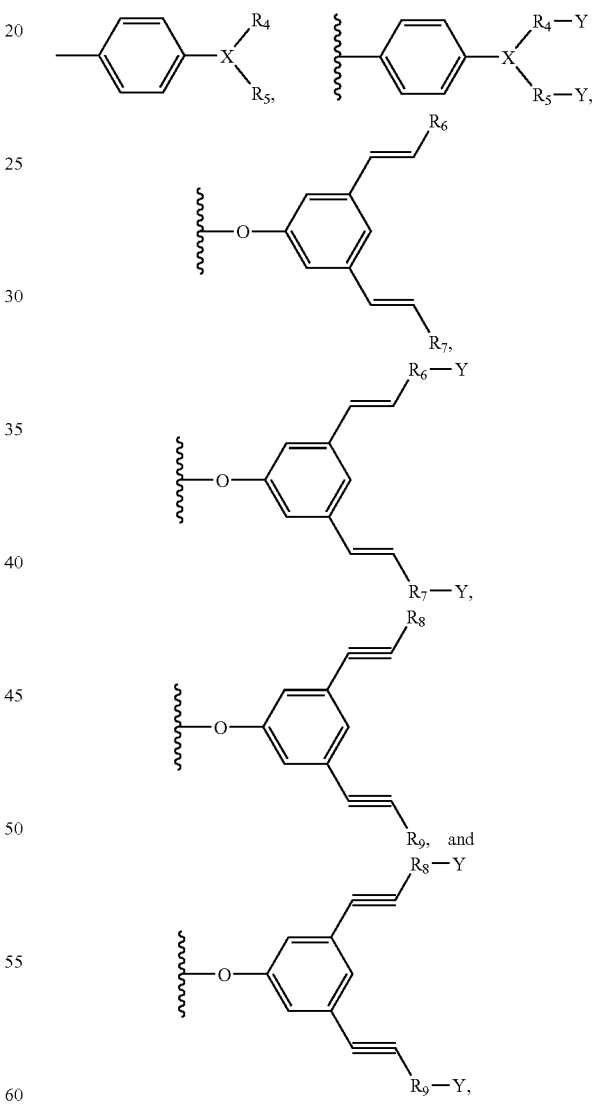

X is —O—, —N, or —S, each of $R_1$, $R_2$, and $R_3$ is one selected from a group consisting of —H, —CH$_3$, —(OCH$_3$), —(OC$_2$H$_5$), and a halogen, and at least one of $R_1$, $R_2$, and $R_3$ is —(OCH$_3$), —(OC$_2$H$_5$), or a halogen, each of $R_4$ and $R_5$ is one selected from a group consisting of —H, —$(CH_2)_n$—OH, —$(CH_2)_n$—$NH_2$, and $(CH_2)_n$—$SH_2$, and $R_4$ and $R_5$ may be identical or different, each of $R_6$, $R_7$, $R_8$, and $R_9$ is one selected from a group consisting of —$(CH_2)_n$—OH, —$(CH_2)_n$—$NH_2$, and —$(CH_2)_n$—$SH_2$, and $R_6$ and $R_7$ may be identical or different, and $R_8$ and $R_9$ may be identical or different, Y is a photodegradable group or an acid degradable group, and l is 2 to 10, m is 1 to 5, and n is 1 to 5.

SN may be represented by

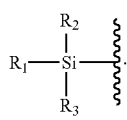

Each of $R_1$, $R_2$, and $R_3$ may be one selected from a group consisting of —H, —$CH_3$, —$(OCH_3)$, —$(OC2H_5)$, and a halogen, and at least one of $R_1$, $R_2$, and $R_3$ may be —$(OCH_3)$, —$(OC_2H_5)$, or a halogen.

When the silicon compound includes Y, a silicon compound according to an exemplary embodiment of the invention may be represented by SN-LS-PL or SN-LS-AL. The PL represents a photodegradable group (PhotoLabile), and the AL represents an acid degradable group (AcidLabile). The PL or AL is coupled to a functional group so as to protect the functional group, and then is degraded by light or acid so as to expose the functional group. Accordingly, the degradation of the PL or AL is referred to as deprotection.

As the PL, various groups, such as the following groups and groups described in U.S. Pat. No. 6,310,189, which is hereby incorporated by reference herein in its entirety, may be used, but these are merely illustrative. Any group may be used insofar as it is degraded by light irradiation and exposes a functional group in a silicon compound.

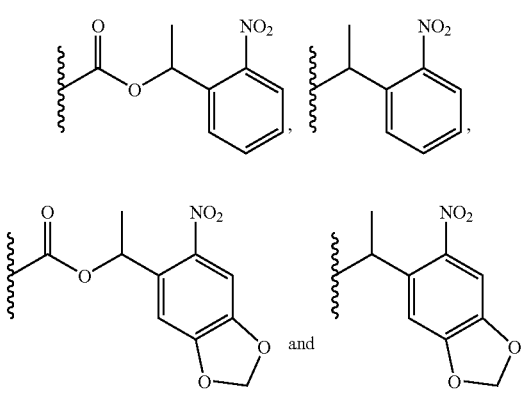

As the AL, the following groups may be used, but these are merely illustrative.

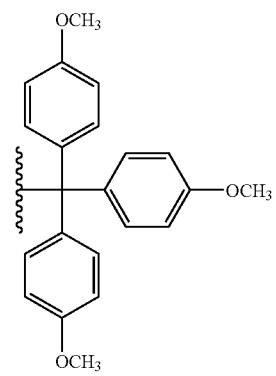

Hereinafter, a method of producing the silicon compound according to an embodiment of the invention will be described. However, the silicon compound according to the embodiment of the invention may be produced by various methods, in addition to the producing method described below.

A silicon compound including A represented by

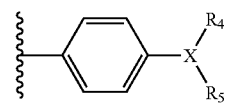

may be produced by the following method.

First, according the following reaction scheme 1, a compound including a functional group to be directly or indirectly coupled to an oligomer probe at its terminal is formed.

<Reaction Scheme 1>

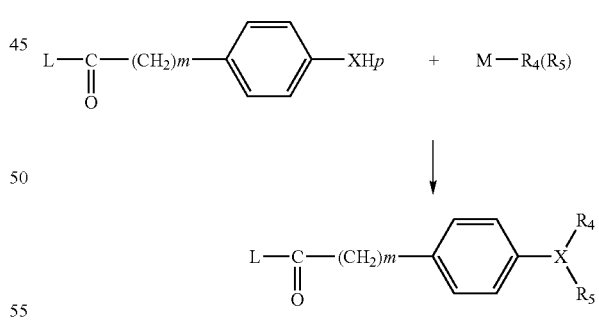

For the reaction scheme 1, L may be one selected from a group consisting of —OH, —ONHS, and a halogen, X may be —H, —N, or —S, and M may be a halogen, each of $R_4$ and $R_5$ may be one selected from a group consisting of —H, —$(CH_2)_n$—OH, —$(CH_2)_n$—$NH_2$, and —$(CH_2)_n$—$SH_2$, and $R_4$ and $R_5$ may be identical or different, m may be 1 to 5, n may be 1 to 5, and p may be 1 or 2.

Next, silicon may be introduced into the compound according to the following reaction scheme 2.

<Reaction Scheme 2>

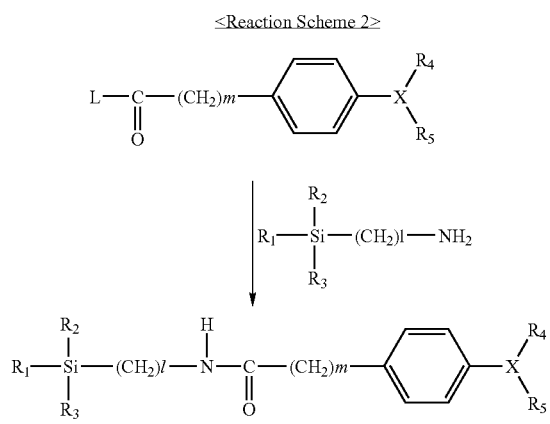

For the reaction scheme 2, l may be 2 to 10, and each of $R_1$, $R_2$, and $R_3$ may be one selected from a group consisting of —H, —CH$_3$, —(OCH$_3$), —(OC$_2$H$_5$), and a halogen, and at least one of $R_1$, $R_2$, and $R_3$ may be —(OCH$_3$), —(OC$_2$H$_5$), or a halogen.

Before the reaction scheme 2, the resultant of the reaction scheme 1 may react with an M-Y material (M is halogen, and Y is a photodegradable group or an acid degradable group) and then reaction scheme 2 progresses, or after the reaction scheme 2, the resultant of the reaction scheme 2 may react with the M-Y material, such that the photodegradable group or the acid degradable group may be introduced into the silicon compound.

A silicon compound including A having an ethylene or acetylene group together with an aromatic compound may be produced by the following method.

First, aromatic carboxylate is produced according to the reaction scheme 3. When aromatic carboxylate exists already, the reaction scheme 3 may be omitted.

<Reaction Scheme 3>

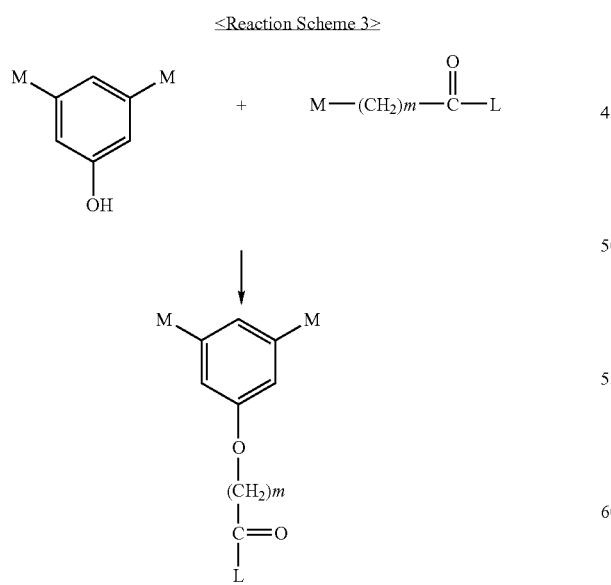

For the reaction scheme 3, L may be one selected from a group consisting of —OH, —ONHS, and a halogen, M may be a halogen, and m may be 1 to 5.

Next, an ethylene or acetylene group including a functional group to be directly or indirectly coupled to an oligomer probe at its terminal is introduced according to the following reaction scheme 4.

<Reaction Scheme 4>

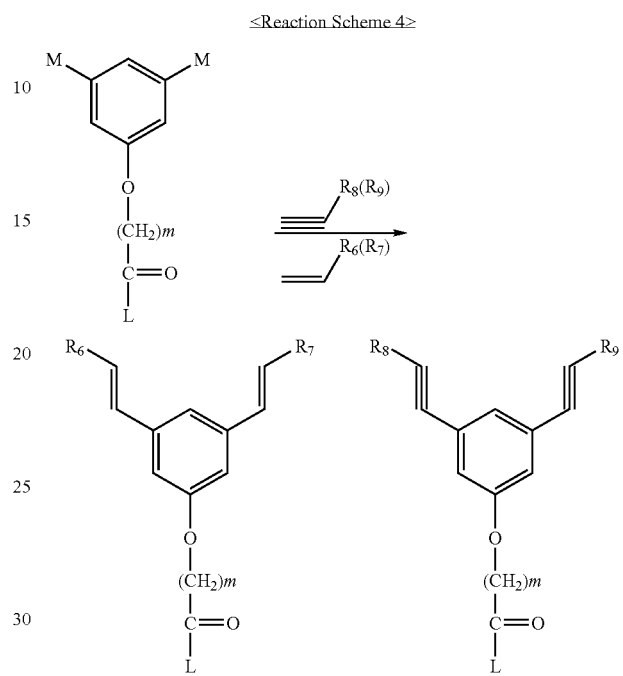

For the reaction scheme 4, each of $R_6$, $R_7$, $R_8$, and $R_9$ may be one selected from a group consisting of —(CH$_2$)$_n$—OH, —(CH$_2$)$_n$—NH$_2$, and (CH$_2$)$_n$—SH$_2$, and $R_6$ and $R_7$ may be identical or different, and $R_8$ and $R_9$ may be identical or different, and n may be 1 to 5.

Finally, silicon may be introduced into the compound according to the following reaction scheme 5.

<Reaction Scheme 5>

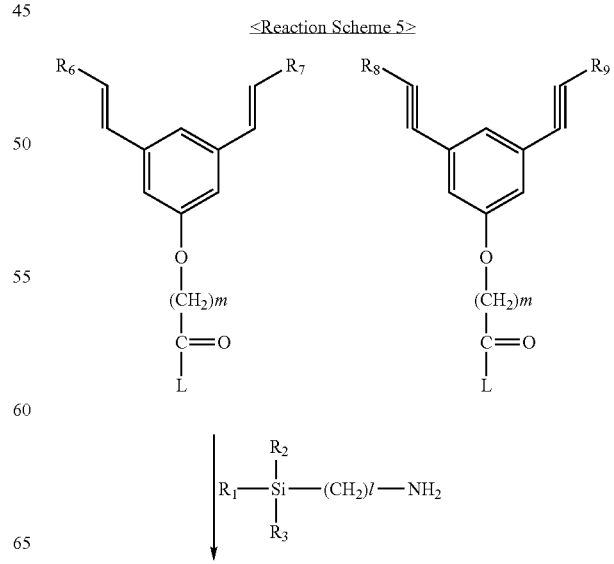

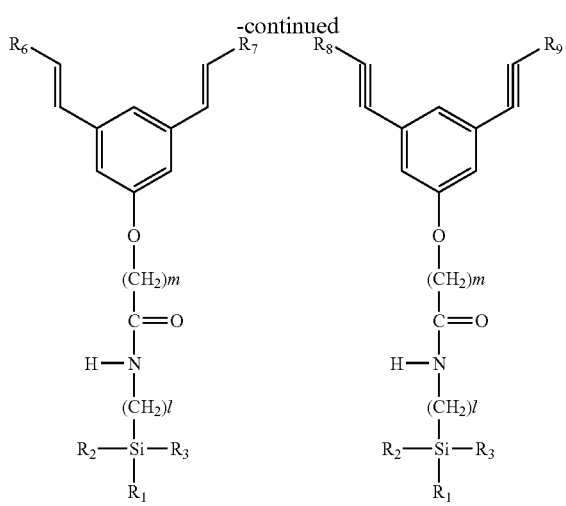
-continued

Hereinafter, a method of manufacturing an oligomer probe array using the above-described silicon compound and an oligomer probe array manufactured accordingly will be described.

Referring to FIG. 1, first, a substrate having a surface to which the silicon compound is coupled is prepared. For example, an active film 120a is formed on the entire surface of the substrate 100. As indicated by an arrow, the active film 120a is patterned so as to form probe cell actives 120 divided by a probe cell separation region 130, which results in increasing an SNR (Signal to Noise Ratio) of an oligomer probe array. That is, in the probe cell separation region 130, the active film 120a is removed, and thus the surface of the substrate 100 is directly exposed. Accordingly, at the surface of the probe cell separation region 130, a functional group to be coupled to an oligomer probe is not included. The formation of the probe cell actives 120 is disclosed in Korean Patent Application Nos. 2006-0039291and 2006-0039716, which are commonly assigned to an assignee of this application, and the disclosure of which is incorporated herein by reference in its entirety.

The substrate 100 may be formed of a material that can minimize an undesirable nonspecific bond during hybridization and further can substantially make the undesirable nonspecific bond zero. Further, the substrate 100 may be formed of a transparent material to visible light and/or ultra-violet (UV). The substrate is a flexible or rigid substrate. The flexible substrate may be a membrane, such as, for example, nylon, nitrocellulose, or the like, or a plastic film. The rigid substrate may be, for example, a silicon substrate, a quartz substrate, a glass substrate, such as soda-lime glass, a substrate having an adjusted pore size, or the like. The silicon substrate, the quartz substrate, the glass substrate, and the like do not almost generate the nonspecific bond during the hybridization. In addition, the glass substrate is beneficial for detection of a fluorescent material as it is transparent to visible light and/or UV. The silicon substrate, the quartz substrate, the glass substrate, and the like are beneficial in that a manufacturing process of various thin films and a photolithography process stably established and used in a manufacturing process of a semiconductor device or a manufacturing process of an LCD panel may be used as they are.

The active film 120a may be formed of a substantially stable material that is not hydrolyzed under a hybridization analysis condition, for example, in contact with phosphate having a pH of about 6 to about 9 or TRIS buffer. Further, the active film 120a may be formed of a material that can be stably formed on the substrate 100 and readily patterned through a semiconductor manufacturing process or an LCD manufacturing process. In addition, the active film 120a may be formed of a material that can directly provide a functional group to be coupled to the silicon compound according to the exemplary embodiment of the invention or can provide a functional group through various surface treatments, such as, for example, an ozone treatment, an acid treatment, a base treatment, and the like. The couplable functional group used herein refers to a group as a starting point of an organic synthesis process. That is, the couplable functional group refers to a group to be covalently bonded or non-covalently bonded. The couplable functional group is not particularly limited insofar as siloxane coupling or organic coupling is possible. For example, the active film 120a may be formed of a silicon oxide film, such as a plasma enhanced tetraethylortho silicate (PE-TEOS) film, a high density plasma (HDP) oxide film, a P—$SiH_4$ oxide film, a thermally oxidized film, or the like, silicate, such as hafnium silicate, zirconium silicate, or the like, a silicon oxynitride film, or a spin-on siloxane film.

Next, the linker including the silicon compound according to the exemplary embodiment of the invention is formed on the active film 120a or the probe cell active 120.

The linker may be formed by coating the above-described silicon compound through once spin coating (first path), or may be formed by forming aminosilane as a reactant of the reaction scheme 2 or the reaction scheme 5 on the entire surface of the substrate 100 and then applying a starting material of the reaction scheme 2 or the reaction scheme 5 to the substrate (second path).

Subsequently, on the substrate on which the linker according to the exemplary embodiment of the invention is formed, an oligomer probe is synthesized by a synthesis method, such as, for example, in-situ photolithography, or an already synthesized oligomer probe is coupled by a spotting method, such that the oligomer probe array is completed. The oligomer probe may be directly coupled to the linker according to the exemplary embodiment of the invention or may be indirectly coupled to the linker through an different linker activated by amidite.

Accordingly, before the oligomer probe is coupled, the photodegradable group or the acid degradable group may exist in the silicon compound. However, before the oligomer probe is coupled, the photodegradable group or the acid degradable group is deprotected. Therefore, the photodegradable group or the acid degradable group does not exist in the resultant oligomer probe array.

The substrate on which the silicon compound film according to the exemplary of the invention is formed is mass-produced and circulated as a preliminary substrate before the oligomer probe is synthesized or spotted. For example, when the silicon compound constituting the linker includes the photodegradable group or the acid degradable group, storage capability of the substrate to which the linker is coupled may be increased.

The details of the embodiments of the invention will be described by way of the following specific experimental examples. The contents which are not described herein can be fully analogized by those skilled in the art, and the descriptions thereof will be omitted.

EXPERIMENTAL EXAMPLE 1

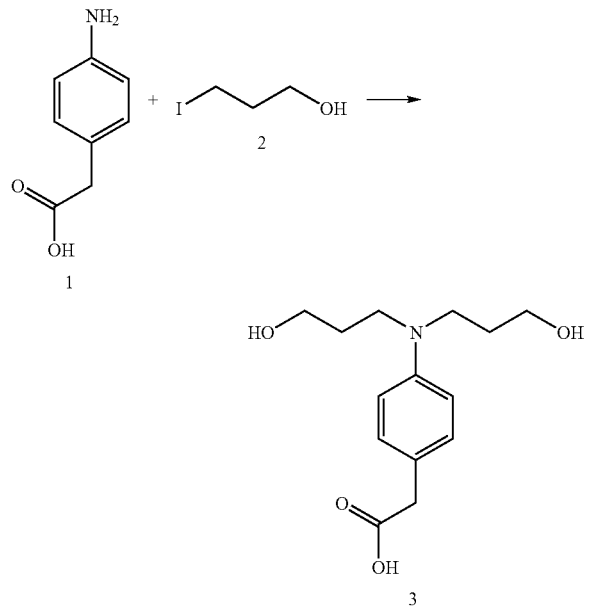

A starting material 1 (about 10 mmol) and triethylamine (about 2 eq) are put in a 100 mL round-bottom two-neck flask and are dissolved into a methanol solvent. Next, a reactant 2 (about 3 mmol) is slowly dropped and added while nitrogen is being purged. The reaction product is moved to an oil bath and then reflux is performed while the temperature gradually rises. For the reaction product, the reflux is continuously performed for about five hours. Then, the reaction product is crystallized using ethylacetate (EtOAc), such that a desired white solid target material 3 is obtained (reaction yield about 85%).

IR (neat): 1619, 3221 cm$^{-1}$

1H NMR (300 MHz, CDCl$_3$+DMSO–d6) δ 7.16 (d, 2H), 6.68 (d, 2H), 3.68 (m, 4H), 3.52 (t, 4H), 3.38 (s, 2H), 3.22 (t, 2H), 1.69 (m, 4H)

EXPERIMENT EXAMPLE 2

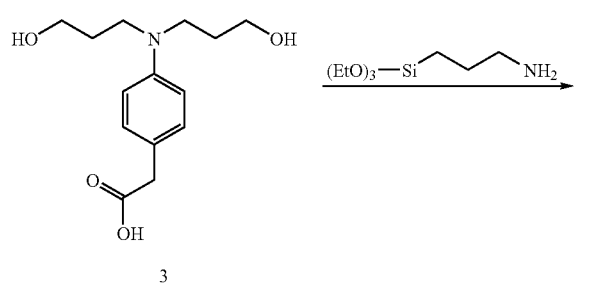

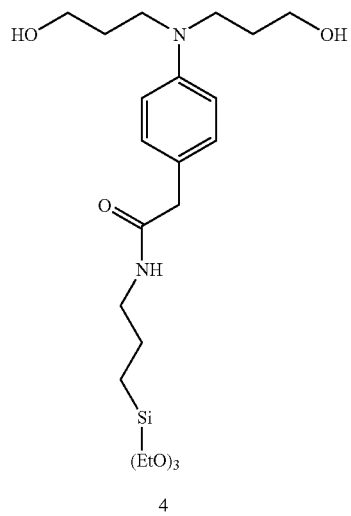

A starting material 3 (about 10 mmol is put in a 100 mL one-neck flask and is dissolved into THF. Next, aminopropyltriethoxysilane and EDC (about 1.5 eq) are put therein, and stirring is performed for about three hours. After the reaction is completed, a precipitate is filtered, then a filtrate is removed under a reduced pressure, and subsequently a residue is washed out using hexane three times. Then, a desired target material 4 is obtained using silica gel column chromatography (EtOAc/ethanol=10/0.5) (yield about 52%).

Rf=0.34(hexane/EtOAc=⅕)

IR (neat): 1452, 1622, 2933, 3221 cm$^{-1}$

1H NMR (300 MHz, CDCl$_3$) δ 7.78 (br, 1H), 7.12 (d, 2H), 6.55 (d, 2H), 3.78-3.61 (m, 10H), 3.49 (t, 2H), 3.31 (s, 2H), 3.19 (t, 2H), 2.63 (m, 2H), 1.64 (m, 6H), 1.25 (t, 9H), 0.66 (m, 2H)

EXPERIMENTAL EXAMPLE 3

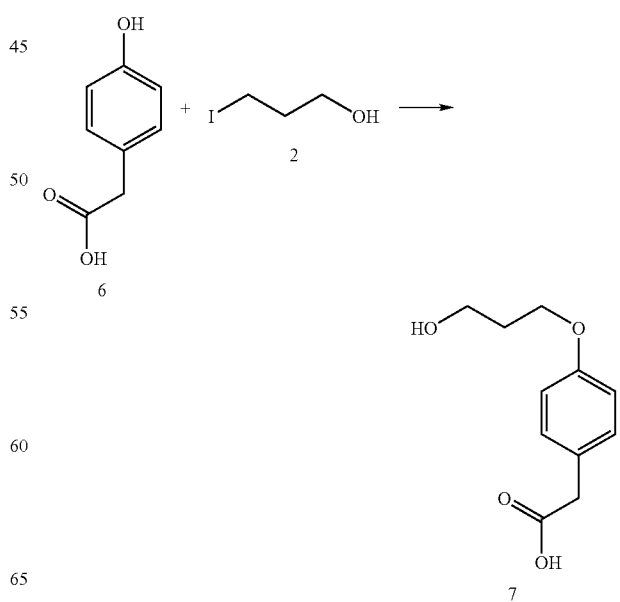

A starting material 6 (about 10 mmol) and triethylamine (about 2 eq) are put in a 100 mL round-bottom two-neck flask and are dissolved into a methanol solvent. Next, a reactant 2 (about 3 mmol) is slowly dropped and added while nitrogen is being purged. The reaction product is moved to oil bath, and a reflux is performed while a temperature gradually rises. For the reaction product, the reflux is continuously performed for about five hours. Then, the reaction product is crystallized using ethylacetate (EtOAc), such that a desired white solid target material 7 is obtained (reaction yield about 85%).

IR (neat): 1632, 2911, 3177 cm$^{-1}$ 1H NMR (300 MHz, CDCl$_3$+DMSO–d6) δ 7.23 (d, 2H), 6.74 (d, 2H), 4.02 (m, 4H), 3.57 (s, 2H), 1.79 (m, 2H), 1.65 (br, 1H)

EXPERIMENTAL EXAMPLE 4

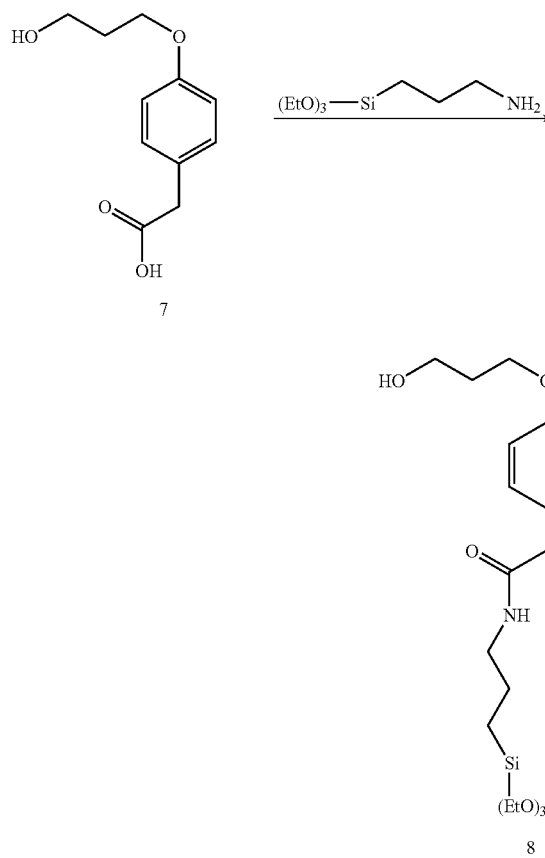

A starting material 7 (about 10 mmol) is put in a 100 mL one-neck flask and is dissolved into THF. Next, aminopropyltriethoxysilane and EDC (about 1.5 eq) are put therein and stirring is performed for about three hours. After the reaction is completed, a precipitate is filtered, then a filtrate is removed under a reduced pressure, and subsequently a residue is washed out using hexane three times. Then, a desired target material 8 is obtained using silica gel column chromatography (EtOAc/ethanol=10/0.5) (yield about 54%).

Rf=0.32 (hexane (Hex)/EtOAc=⅕)

IR (neat): 1432, 1655, 2933 cm$^{-1}$

1H NMR (300 MHz, CDCl$_3$) δ 7.23 (d, 2H), 6.74 (d, 2H), 4.02 (m, 4H), 3.74 (q, 6H), 3.57 (s, 2H), 2.62 (m, 2H), 1.79 (m, 2H), 1.65 (br, 1H), 1.53 (m, 2H), 1.24 (t, 9H), 0.61 (m, 2H)

EXPERIMENTAL EXAMPLE 5

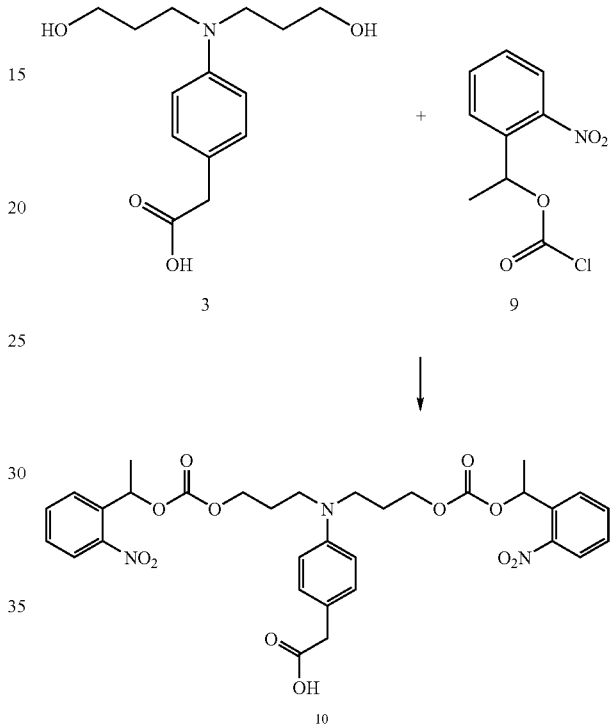

A starting material 3 (about 1 mmol) is put in a 100 mL one-neck flask, then is dissolved into an acetonitrile (ACN) solvent (about 50 mL), and subsequently is rapidly moved to a cold salt bath. A reactant 9 (about 2.5 eq) is dissolved into ACN (about 5 mL) and is slowly dropped and added into the cold salt bath. Next, triethylamine (about 2 eq) is added. The reaction product is continuously subject to reaction under a nitrogen atmosphere for about four hours while a temperature gradually rises to a normal temperature. The completion of the reaction is checked by thin film chromatography (TLC). The reaction completed solvent is distilled under a reduced pressure, and the reaction product is dissolved using EtOAc (about 100 mL). Next, the reaction product is washed using NaHCO$_3$ (sat, aq, about 100 mL) one time and subsequently is washed using NaCl (sat, aq, about 100 mL) one time. An organic layer is dried using sodium sulfate anhydride, then is filtered, and subsequently is distilled under a reduced pressure. Then, a desired solid target compound 10 is obtained from a crude compound using silica gel column chromatography (EtOAc:Hex:MeOH=5:1:0.05, Rf: 0.5) (yield about 75%).

EXPERIMENTAL EXAMPLE 6

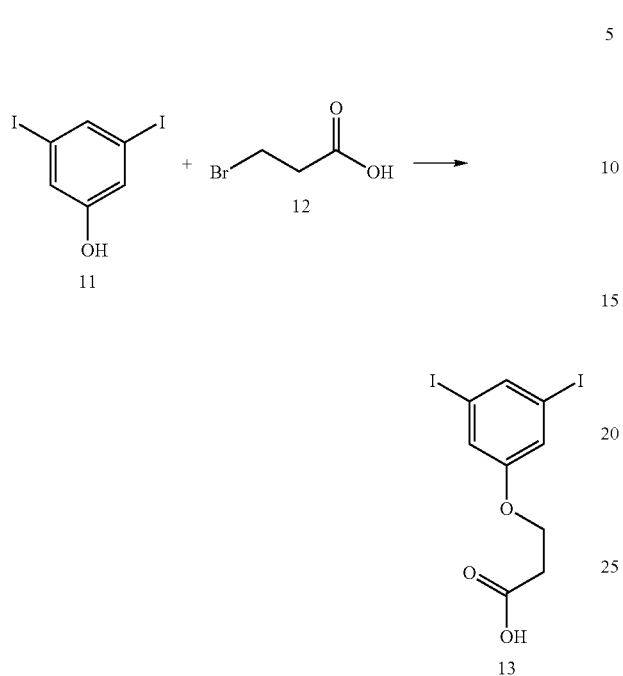

A starting material 11 (about 1 mmol) is dissolved into a methanol solvent at a normal temperature, then a reactant 12 (about 1.01 eq) is put therein, and subsequently NaOMe (about 1.5 eq) is gradually added. All reactions progress under a nitrogen atmosphere. After the completion of the reaction is checked by the TLC, water (about 1 mL) is added to the reaction product so as to quench the reaction. Next, the solvent is distilled under a reduced pressure, and the reaction product is solidified using EtOAc and is re-crystallized using EtOAc and hexane, such that a white solid target compound 13 is obtained (yield about 65%).

EXPERIMENTAL EXAMPLE 7

A starting material 13 (about 10 mmol) is put in a round-bottom flask and is dissolved into a DMF (about 30 mL) solvent. Next, about 5% Pd(OAc)$_2$, about 1 eq LiCl, and about 1.2 eq KOAc are slowly put in the reaction solution, and then a reactant 14 (about 3.0 eq) is added. The reaction product is moved to an oil bath and is subject to reaction at about 60° C. for about four hours. The completion of the reaction is checked using the TLC. After the reaction is completed, water (about 1 mL) is added so as to quench the reaction, and the reaction product is extracted using NH$_4$Cl (aq, sat, about 50 mL) and EtOAc (about 50 mL). Next, an organic layer is washed using NaCl (sat, aq, about 100 mL) one time, then is dried using sodium sulfate anhydride, subsequently is filtered, and finally is distilled under a reduced pressure. Then, a desired target compound 15 is obtained from a crude compound using silica gel column chromatography (Hex:EtOAc:MeOH=1:4:0.05) (yield about 66%).

EXPERIMENTAL EXAMPLE 8

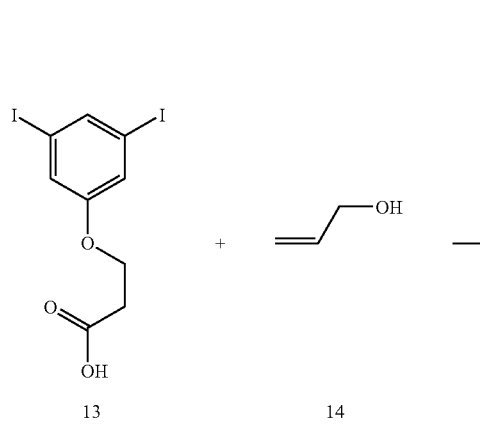

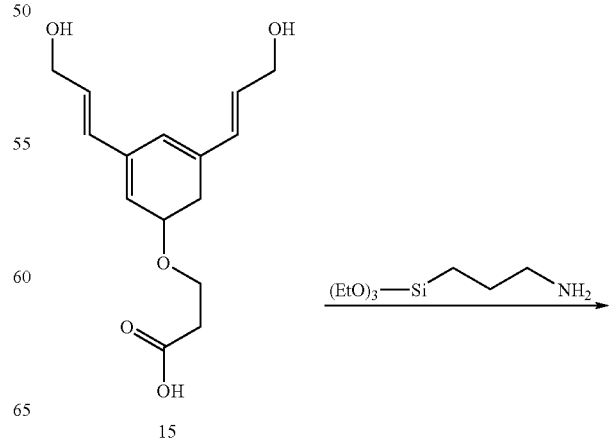

-continued

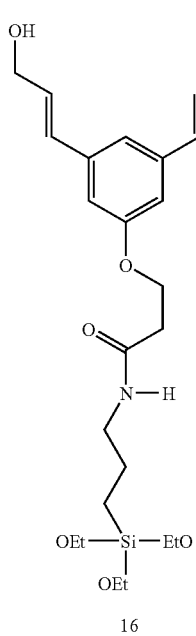

16

A starting material 15 (about 10 mmol) is put in a 100 mL one-neck flask and is dissolved into THF. Next, aminopropyltriethoxysilane and EDC (about 1.5 eq) are put therein and stirring is performed for about three hours. After the reaction is completed, a precipitate is filtered, then a filtrate is removed under a reduced pressure, and subsequently a residue is washed out using hexane three times. Then, a desired target material 16 is obtained using silica gel column chromatography (EtOAc/ethanol=10/0.5) (yield about 67%).

EXPERIMENTAL EXAMPLE 9

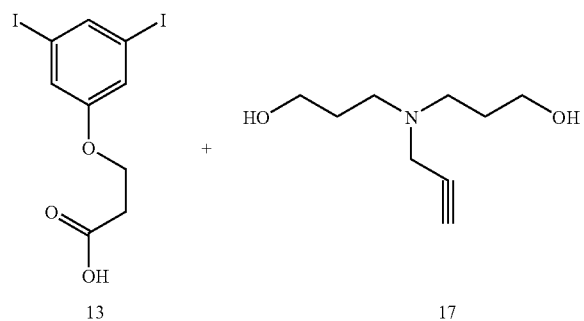

-continued

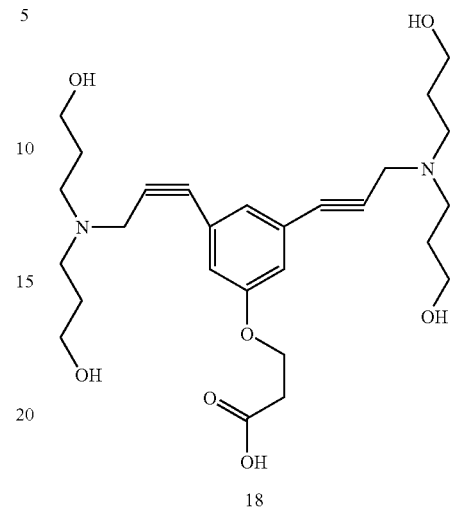

18

First, a reactant 17 is prepared as follows. Propargylamine (about 1 mmol) is put in a pressure tube at a normal temperature, then bronopropanol (about 2.5 eq) is put therein, and subsequently is dissolved into a methanol solvent. Subsequently, after a cover is sealed, the reaction product is moved to an oil bath, and is stirred at about 130° C. for about eight hours. Next, after a temperature of the reaction product falls to a normal temperature, the solvent is distilled under a reduced pressure, and then a crude reactant 17 is obtained.

Next, at a normal temperature, a starting material 13 (about 10 mmol) is put in a round-bottom flask and is dissolved into a DMF (about 30 mL) solvent. About 5% Pd(OAc)$_2$, about 1 eq LiCl, and about 1.2 eq KOAc are slowly put in the reaction solution, and then the crude reactant 17 (about 3.0 eq) is added. The reaction produce is moved to an oil bath and then is subject to reaction at about 60° C. for about six hours. The completion of the reaction is checked using the TLC. After the reaction is completed, water (about 1 mL) is added so as to quench the reaction, and then a crude reaction product is obtained through distillation under a reduced pressure. Next, the reaction product is washed using EtOAc three time, and then a desired target compound 18 is obtained using silica gel column chromatography (Hex:EtOAc:MeOH=1:4:0.05) (yield about 61%).

EXPERIMENTAL EXAMPLE 10

A starting material 18 (about 10 mmol) is put in a 100 mL one-neck flask and is dissolved into THF. Next, aminopropyltriethoxysilane and EDC (about 1.5 eq) are put therein and stirring is performed for about three hours. After the reaction is completed, a precipitate is filtered, then a filtrate is removed under a reduced pressure, and subsequently a residue is washed out using hexane three times. Then, a desired silicon compound is obtained using silica gel column chromatography (EtOAc/ethanol=10/0.5) (yield about 69%).

EXPERIMENTAL EXAMPLE 11

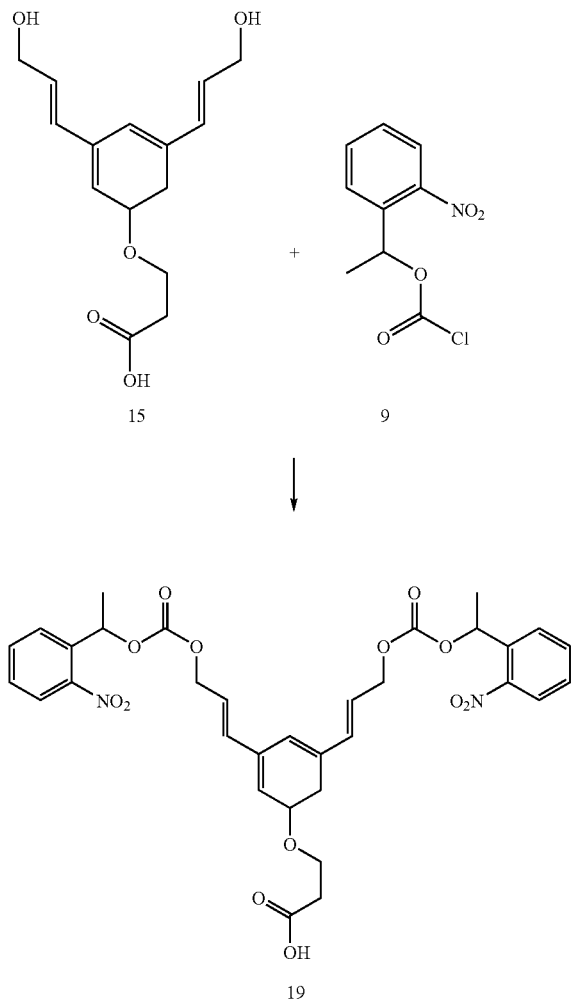

A starting material 15 (about 1 mmol) is put in a 100 mL one-neck flask, then is dissolved in an ACN (about 50 mL) solvent, and subsequently is moved to a cold salt bath. Next, the reactant 9 (about 2.5 eq) is dissolved into ACN (about 5 mL) and then is slowly dropped and added into the cold salt bath. Next, triethylamine (about 2 eq) is added. The reaction product is continuously subject to reaction under a nitrogen atmosphere for about four hours while the temperature gradually rises to a normal temperature. The completion of the reaction is checked using the TLC. The reaction completed solvent is distilled under a reduced pressured, and the reaction product is dissolved using EtOAc (about 100 mL). Then, the reaction product is washed by $NaHCO_3$ (sat, aq, about 100 mL) one time and subsequently is washed using NaCl (sat, aq, about 100 mL) one time. An organic layer is dried using sodium sulfate anhydride, then is filtered, and subsequently is distilled under a reduced pressure. Then, a desired solid target compound 19 is obtained from the crude compound using silica gel column chromatography (EtOAc:Hex:MeOH=2:1: 0.03, Rf: 0.31) (yield about 59%).

EXPERIMENTAL EXAMPLE 12

The silicon compound produced in the experimental example 2 is applied onto the probe cell active having a spin-on siloxane film pattern on the silicon substrate so as to form a linker.

As a comparative example, known aminopropyltriethoxysilane is applied to the substrate formed in the same manner so as to form a linker.

Figure 2:
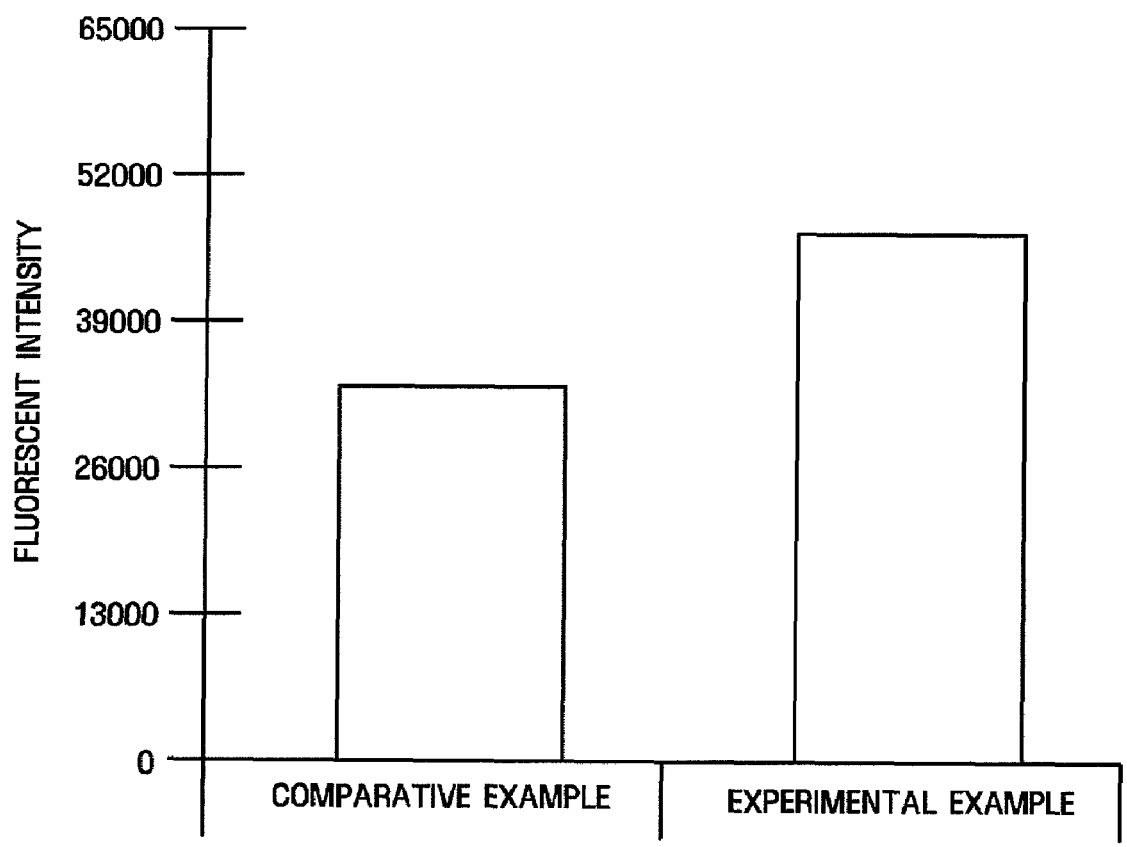
FIG. 2 is a graph showing fluorescent intensities measured after linkers are formed using a silicon compound according to an exemplary embodiment of the invention and a known linear silicon compound.

Next, after $Cy_3$ labeling, a fluorescent intensity is measured using a CCD. The result is shown in FIG. 2. From the result of FIG. 2, it can be seen that, when the silicon compound according to each of the experimental examples of the invention is used, the fluorescent intensity increases. Therefore, it can be seen that the silicon compound according to each of the experimental example of the invention is more efficient for coupling to the oligomer probe.

As the non-linear silicon compound according to the exemplary embodiment of the invention includes the aromatic compound, it is rarely affected by a solvent upon a sol-gel reaction compared with a linear compound. Accordingly, self aggregation is significantly reduced, and thus a uniform monolayer can be formed. Therefore, a stable linker can be formed. As a result, upon hybridization analysis, the fluorescent intensity can be increased.

Having described the exemplary embodiments of the present invention, it is further noted that it is readily apparent to those of reasonable skill in the art that various modifications may be made without departing from the spirit and scope of the invention which is defined by the metes and bounds of the appended claims.

What is claimed is:

1. A silicon compound that is represented by the following formula

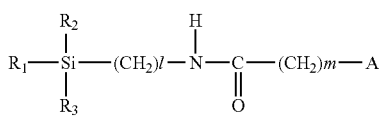

in the formula, A is an aromatic group selected from a group consisting of

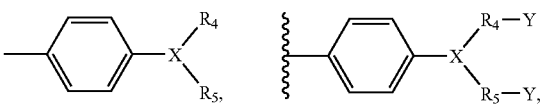

-continued

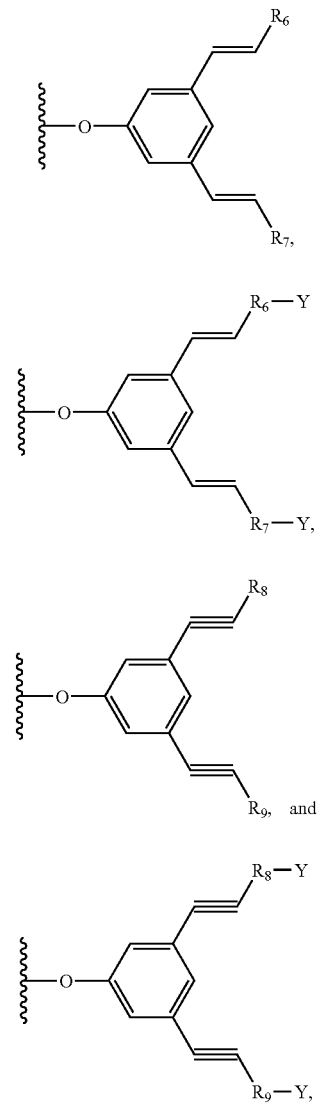

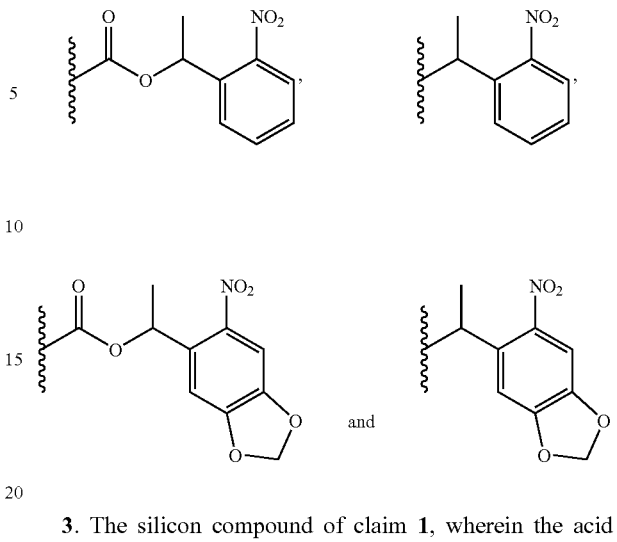

3. The silicon compound of claim 1, wherein the acid degradable

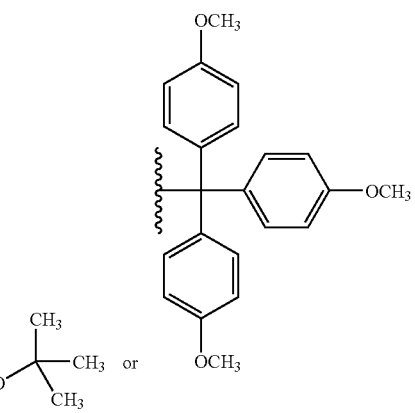

X is —O—, —N—, or —S—, each of $R_1$, $R_2$, and $R_3$ is one selected from a group consisting of —H, —CH$_3$, —(OCH$_3$), —(OC$_2$H$_5$), and a halogen, and at least one of $R_1$, $R_2$, and $R_3$ is —(OCH$_3$), —(OC$_2$H$_5$), or a halogen, each of $R_4$ and $R_5$ is one selected from a group consisting of —H, —(CH$_2$)$_n$—OH, —(CH$_2$)$_n$—NH$_2$, and —(CH$_2$)$_n$—SH$_2$, and $R_4$ and $R_5$ may be identical or different, each of $R_6$, $R_7$, $R_8$, and $R_9$ is one selected from a group consisting of —(CH$_2$)$_n$—OH, —(CH$_2$)$_n$—NH$_2$, and —(CH$_2$)$_n$—SH$_2$, and $R_6$ and $R_7$ may be identical or different, and $R_8$ and $R_9$ may be identical or different, Y is a photodegradable group or an acid degradable group, and l is 2 to 10, m is 1 to 5, and n is 1 to 5.

2. The silicon compound of claim 1, wherein the photodegradable group is one selected from a group consisting of 4. A method of manufacturing an oligomer probe array, comprising:

providing a substrate;

forming an active film on the substrate;

forming a silicon compound film on the substrate, the silicon compound being represented by the following formula

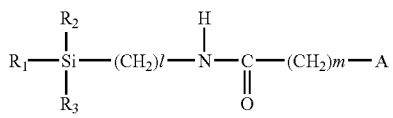

in the formula, A is an aromatic group selected from a group consisting of

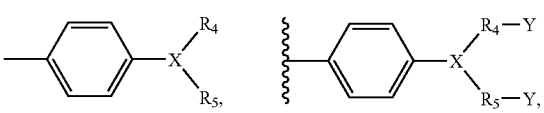

-continued

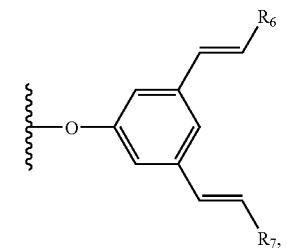

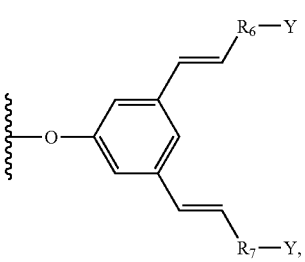

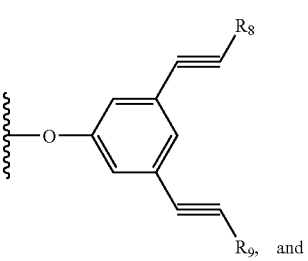

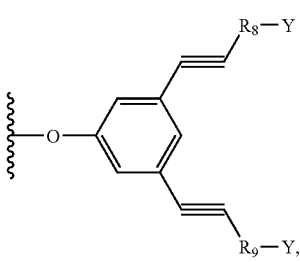

X is —O, —N, or —S, each of $R_1$, $R_2$, and $R_3$ is one selected from a group consisting of —H, —$CH_3$, —($OCH_3$), —($OC_2H_5$), and a halogen, and at least one of $R_1$, $R_2$, and $R_3$ is —($OCH_3$), —($OC_2H_5$), or a halogen, each of $R_4$ and $R_5$ is one selected from a group consisting of —H, —$(CH_2)_n$—OH, —$(CH_2)_n$—$NH_2$, and $(CH_2)_n$—$SH_2$, and $R_4$ and $R_5$ may be identical or different, each of $R_6$, $R_7$, $R_8$, and $R_9$ is one selected from a group consisting of —$(CH_2)_n$—OH, —$(CH_2)_n$—$NH_2$, and —$(CH_2)_n$—$SH_2$, and $R_6$ and $R_7$ may be identical or different, and $R_8$ and $R_9$ may be identical or different, Y is a photodegradable group or an acid degradable group, and l is 2 to 10, m is 1 to 5, and n is 1 to 5.

5. The method of claim 4, wherein the photodegradable group is one selected from a group consisting of

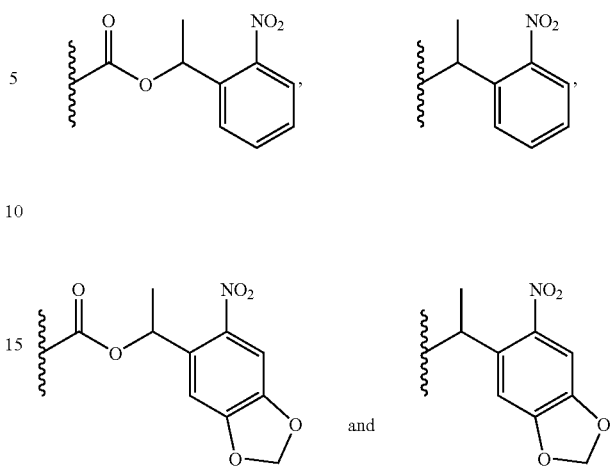

6. The method of claim 4, wherein the acid degradable group is

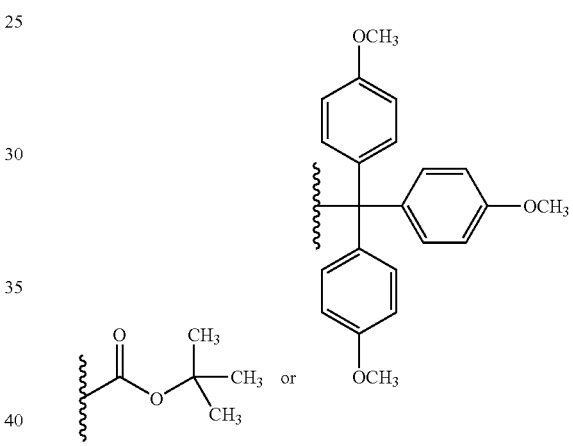

7. The method of claim 4, further comprising, before the forming of the silicon compound film:
patterning the active film so as to form probe cell actives divided by a probe cell separation region having an exposed region of the substrate.

8. The method of claim 7, wherein the substrate is a silicon substrate or a glass substrate.

9. The method of claim 4, wherein the active film includes a silicon oxide film, a thermally oxidized film, silicate, a silicon oxynitride film, or a spin-on siloxane film.

10. The method of claim 4, further comprising, after the forming of the silicon compound film;
synthesizing an oligomer probe using in-situ photolithography or spotting an already synthesized oligomer probe.

11. The method of claim 10, further comprising, before the synthesizing or the spotting:
forming a different linker activated by amidite on the silicon compound film.

12. A substrate for an oligomer probe array, comprising:
a substrate;
an active film on the substrate; and
a linker formed of a silicon compound represented by the following formula on the active film

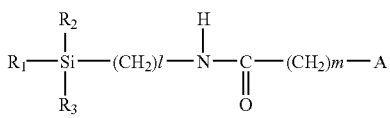

in the formula, A is an aromatic group selected from a group consisting of

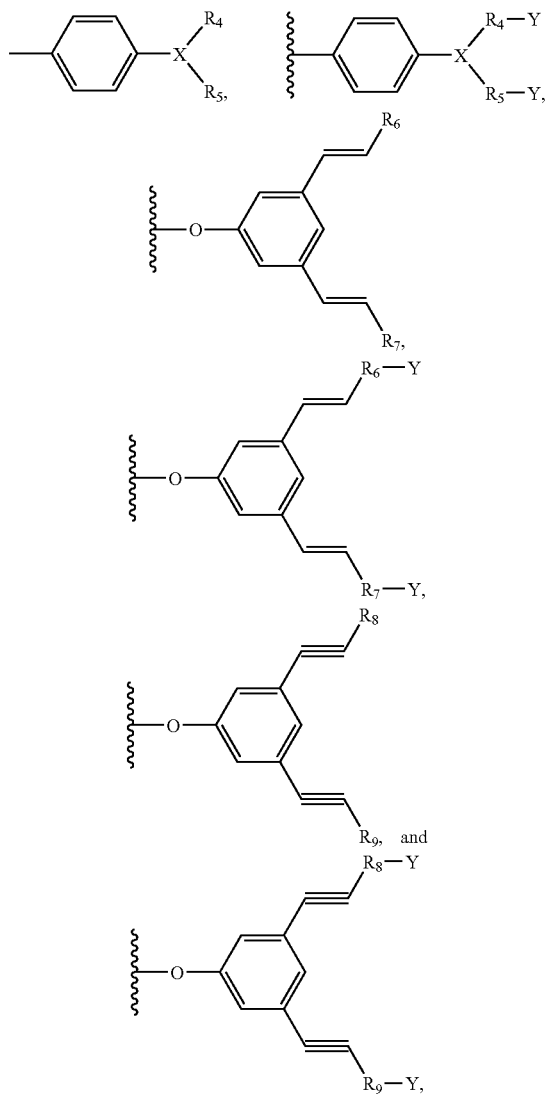

X is —O—, —N—, or —S—, each of $R_1$, $R_2$, and $R_3$ is one selected from a group consisting of —H, —$CH_3$, —($OCH_3$), —($OC_2H_5$), and a halogen, and at least one of $R_1$, $R_2$, and $R_3$ is —($OCH_3$), —($OC_2H_5$), or a halogen, each of $R_4$ and $R_5$ is one selected from a group consisting of —H, —$(CH_2)_n$—OH, —$(CH_2)_n$—$NH_2$, and —$(CH_2)_n$—$SH_2$, and $R_4$ and $R_5$ may be identical or different, each of $R_6$, $R_7$, $R_8$, and $R_9$ is one selected from a group consisting of —$(CH_2)_n$—OH, —$(CH_2)_n$—$NH_2$, and —$(CH_2)_n$—$SH_2$, and $R_6$ and $R_7$ may be identical or different, and $R_8$ and $R_9$ may be identical or different, Y is a photodegradable group or an acid degradable group, and l is 2 to 10, m is 1 to 5, and n is 1 to 5.

13. The substrate of claim 12, wherein the photodegradable group is one selected from a group consisting of

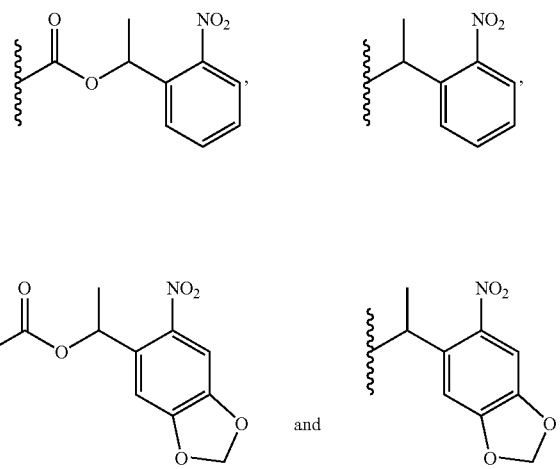

14. The substrate of claim 12, wherein the acid degradable group is

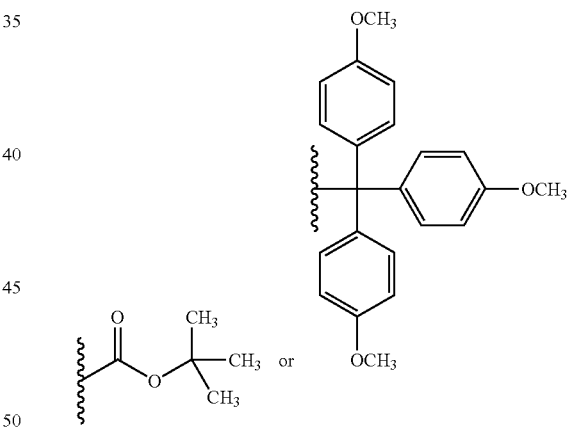

15. The substrate of claim 12, further comprising:
a probe cell separation region that divides the active film into a plurality of probe cell actives, and does not include a functional group to be coupled to the oligomer probe at its surface.

16. The substrate of claim 15, wherein the probe cell separation region is an exposed surface of a silicon substrate or a glass substrate.

17. An oligomer probe array comprising:
a substrate;
an active film on the substrate;
a linker formed of a silicon compound represented by the following formula on the active film;

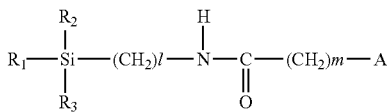

in the formula, A is an aromatic group selected from a group consisting of

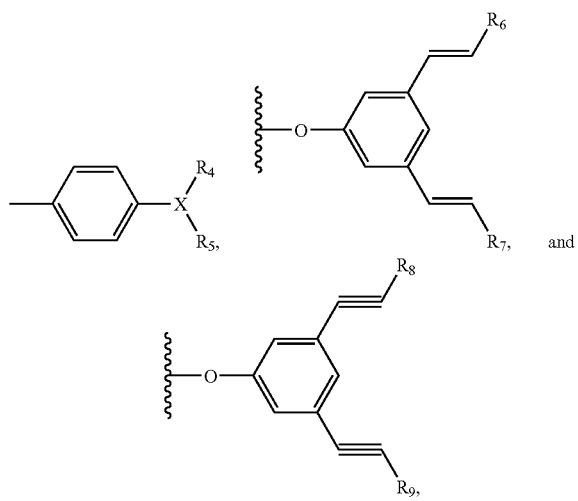

X is —O, —N, or —S, each of $R_1$, $R_2$, and $R_3$ is one selected from a group consisting of —H, —CH$_3$, —(OCH$_3$), —(OC$_2$H$_5$), and a halogen, and at least one of $R_1$, $R_2$, and $R_3$ is —(OCH$_3$), —(OC$_2$H$_5$), or a halogen, each of $R_4$ and $R_5$ is one selected from a group consisting of —H, —(CH$_2$)$_n$—OH, —(CH$_2$)$_n$—NH$_2$, and (CH$_2$)$_n$—SH$_2$, and $R_4$ and $R_5$ may be identical or different, each of $R_6$, $R_7$, $R_8$, and $R_9$ is one selected from a group consisting of —(CH$_2$)$_n$—OH, —(CH$_2$)$_n$—NH$_2$, and —(CH$_2$)$_n$—SH$_2$, and $R_6$ and $R_7$ may be identical or different, and $R_8$ and $R_9$ may be identical or different, and l is 2 to 10, m is 1 to 5, and n is 1 to 5; and an oligomer probe coupled to the linker.

18. The oligomer probe array of claim 17, further comprising:
a probe cell separation region that divides the active film into a plurality of probe cell actives, and does not have a functional group to be coupled to the oligomer probe at its surface.

19. The oligomer probe array of claim 18, wherein the probe cell separation region is an exposed surface of a silicon substrate or a glass substrate.

20. The oligomer probe array of claim 17, wherein the active film includes a silicon oxide film, a thermally oxidized film, silicate, a silicon oxynitride film, or a spin-on siloxane film.

21. The oligomer probe array of claims 17, wherein the oligomer probe is coupled to the linker through a different linker activated by amidite.

22. The method of claim 9, wherein the active film includes the silicon oxide film and wherein the silicon oxide film is selected from the group consisting of a PE-TEOS film, an HDP oxide film, or a P—SiH$_4$ oxide film.

23. The method of claim 9, wherein the active film includes the silicate and wherein the silicate is selected from the group consisting of hafnium silicate or zirconium silicate.

24. The method of claim 20, wherein the active film includes the silicon oxide film and wherein the silicon oxide film is selected from the group consisting of a PE-TEOS film, an HDP oxide film, or a P—SiH$_4$ oxide film.

25. The method of claim 20, wherein the active film includes the silicate and wherein the silicate is selected from the group consisting of hafnium silicate or zirconium silicate.

* * * * *